United States Patent [19]

Sales

[11] Patent Number: 5,439,931

[45] Date of Patent: Aug. 8, 1995

[54] METHOD FOR INCREASING LIBIDO IN POST-MENOPAUSAL WOMEN

[75] Inventor: James J. Sales, Indianapolis, Ind.

[73] Assignee: Eli Lilly and Company, Indianapolis, Ind.

[21] Appl. No.: 171,329

[22] Filed: Dec. 21, 1993

[51] Int. Cl.$^6$ ............................................. A61K 31/38
[52] U.S. Cl. .................................................... 514/443
[58] Field of Search ........................................ 514/443

[56] References Cited

U.S. PATENT DOCUMENTS

| 4,133,814 | 1/1979 | Jones et al. | 260/326.55 |
| 4,380,635 | 4/1983 | Peters | 546/202 |
| 4,418,068 | 11/1983 | Jones | 424/267 |
| 5,075,321 | 12/1991 | Schreiber | 514/317 |

FOREIGN PATENT DOCUMENTS

WO93/10113 5/1993 WIPO.
WO93/1074 6/1993 WIPO.

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.
Bryant et al., "Protection from Bone Loss and Lowering of Serum Cholesterol in the Absence of Uterine Stimulation in Ovariectomized Rats", Am Soc. Bone & Min. Res., Tampa, Sep. 18-22, 1993.
Bryant et al., "Raloxifene is a Tissue Specific Estrogen Agonist", Am Soc. Bone & Min. Res., Tampa, Sep. 18-22, 1993.
Frolick et al., "In Vivo and In Vitro Metabolism of Raloxifene", Am. Soc. Bone & Min. Res., Tampa, Sep. 18-22, 1993.
Glasebrook et al., "Multiple Binding Sites for the Anti--estrogen Raloxifene", Am Soc. Bone & Min. Res., Tampa, Sept. 18-22, 1993.
Hock et al., "Combination of Raloxifene and Human Parathyoid Hormone 1-34; Increased Femur Bone Mass in Young Ovariectomized (OVX) Rats", Am. Soc. Bone & Min. Res., Tampa, Sep. 18-22, 1993.
Sato et al., "DEXA Analysis of Raloxifene Effects in the Bones From Ovariectomized Rats", Am. Soc. for Bone and Min. Res., Tampa, Sep. 18-22, 1993.
Yang et al., "Raloxifene an Anti-Estrogen, Simulates the Effects of Estrogen in Inhibiting Bone Resorption Through Regulating TGFB-3 Expression in Bone;" Am Soc. for Bone and Min. Res., Tampa, Sep. 18-22, 1993.

(List continued on next page.)

Primary Examiner—Zohreh Fay
Attorney, Agent, or Firm—James J. Sales

[57] ABSTRACT

A method of increasing libido in post-menopausal women comprising administering to a female human in need of treatment an effective amount of a compound having the formula

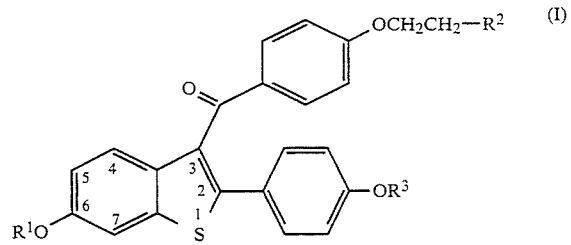

wherein $R^1$ and $R^3$ are independently hydrogen, $-CH_3$,

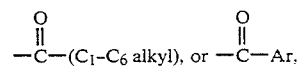

wherein Ar is optionally substituted phenyl;

$R^2$ is selected from the group consisting of pyrrolidine, hexamethyleneimino, and piperidino; or a pharmaceutically acceptable salt of solvate thereof.

3 Claims, No Drawings

OTHER PUBLICATIONS

Black et al., "Distinct, Structure-Related Profiles of Estrogenic and Anti-Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109;1981, 987–989.

Black, L. J. "Biological Actions and Binding Properties of a New Estrogen Antagosist LY117018," In: Homone Antagonists, 129–82, 1982 (M.K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derives Antiestrogen, Life Sciences, 32:1983. 1031–1036.

Black et al., The Relationship of the Antiestrogenic Efficacy of LY156758 to its Pharmacokinetics and Metabolism Following Oral Adminstration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl) ethoxyl]–phenyl] methanone, methanesultonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)-benzo[b]thien–3–yl][4–(1–piperidinyl)ethoxy]–phenyl]-methanone Hydrochloride (LY156758), a Remarkably Effective Estrogen Antagonist with Only Minimal Intrinsic Estrogenicity, J. Med. Chem. 27(8), 1984, 1057–1066.

METHOD FOR INCREASING LIBIDO IN POST-MENOPAUSAL WOMEN

BACKGROUND OF THE INVENTION

Due to the advancements in medical science, along with education, the quality and length of life have both been increased. As a result, the population, as a whole, is living longer. As such, situations which have been present but not in great numbers are becoming more numerous and recognized.

One of those situations which has been present but possibly not given enough weight is sexuality in old age. While there has always been some thought that old people are incapable of engaging in sexual activities, which is somewhat supported by a definite decline in sexuality for both sexes as they get older, sexual activity among the elderly cannot be ignored. Therefore, problems associated with such activity also can not be ignored.

While the male, from the early and middle years, has a relatively steady decline in sexual capacity and activity, the same cannot be as convincingly said about women. There are reports that the sexual capacity of the female does not change much until late in life. (Kinsey, A. C., et al., Sexual Behavior in the Human Female, Saunders, PA., pg. 353 (1953)). In particular, libido decreases substantially in a considerable percentage of cases after the menopause (Lauritzen et al., Estrogen Therapy the Benefits and Risks, 3rd International Workshop on Estrogen Therapy in Geneva, Oct. 20–21, 1977, Frontiers of Hormone Research, Vol. 5, pg. 10 (1978)). This belief is supported by Pfeiffer, E., et al., Terminus of Sexual Behavior in Middle and Old Age, Journal of the American Geriatric Society, pg. 2151–2158 (1972), and Pfeiffer et al., Sexual Behavior in Middle Life, American Journal of Psychiatry, 128, 1262–1267 (1972). In the Pfeiffer studies, a much greater decline in both sexual activity and interest among women between the ages of 45 and 71 was found as compared to men the same age, and the most dramatic change took place between 50–60 years of age, which is, of course, generally the period during which women experience menopause or are post-menopausal. In the age group of 66–71, 50% of women said they had no or little sexual interest compared with 10% of men in the same age group.

While there has been no direct link between declining estrogen levels and declining sexuality, it has been stated that hormonal changes following a natural menopause, and certainly following surgical menopause, may contribute to the sexual decline in a portion of women. Exactly how menopause contributes to the loss of libido is not understood, yet seems fairly evident. (Bancroft, Human Sexuality and Its Problems, 2nd ed., pg. 292–293, (1989)). Therefore, it would be of use to find compounds which increase libido in post-menopausal women.

SUMMARY OF THE INVENTION

This invention provides methods for increasing libido in post-menopausal women, comprising administering to a human in need of treatment an effective amount of a compound of formula I

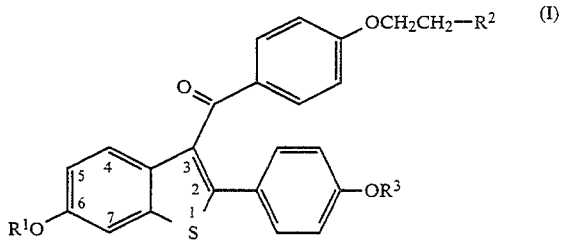

Wherein $R^1$ and $R^3$ are independently hydrogen, $-CH_3$,

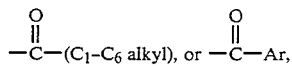

wherein Ar is optionally substituted phenyl;

$R^2$ is selected from the group consisting of pyrrolidino, hexamethyleneimino and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for increasing libido. The methods of treatment provided by this invention are practiced by administering to a human in need a dose of a compound of formula I or a pharmaceutically acceptable salt or solvate thereof, that is effective to increase libido.

The term "post-menopausal women" is defined to include not only women of advanced age who have passed through menopause, but also women who have been hysterectomized or for some other reason have suppressed estrogen production, such as those who have undergone long-term administration of corticosteroids, suffer from Cushions' syndromes or have gonadal dysgenesis.

Raloxifene, one of the compounds of the invention, is the hydrochloride salt of a compound of formula 1 wherein $R^1$ and $R^3$ are both hydrogen and $R^2$ is 1-piperidinyl, Raloxifene is a nuclear regulatory molecule. Raloxifene has been shown to bind to the estrogen receptor and it was originally thought to be a molecule whose function and pharmacology was that of an anti-estrogen in that it blocked the ability of estrogen to activate uterine tissue and estrogen-dependent breast cancers. Indeed, raloxifene does block the action of estrogen in some cells; however, in other cell types, raloxifene activates the same genes as estrogen does and displays the same pharmacology, e.g., osteoporosis and hyperlipidemia. As a result, raloxifene has been referred to as an anti-estrogen with mixed agonist-antagonist properties. The unique profile which raloxifene displays and differs from that of estrogen is now thought to be the unique activation and/or suppression of various gene functions by the raloxifene estrogen receptor complex as opposed to activation and/or suppression of genes by the estrogen receptor complex. Therefore, although raloxifene and estrogen utilize the same receptor, the pharmacological outcome from gene regulation of the two is not easily predicted and is unique to each.

The expression "libido" as used herein refers to those aspects of the human psyche which are related to sexual interest and drive. Additionally, the expression "libido" refers to related psychic attitudes concerned with mental well-being and which refer to such characteristics as mental alertness and activity, creativity, enthusiasm, sociability and an awareness of interpersonal relationships. Libido is generally recognized to be the result of a complex interaction of factors in which genetic, anatomic, neurologic, psychologic and biochemical factors all plan prominent roles. The exact mechanism by which the compounds of the present invention achieve this effect is not understood except to the extent that it is attributable to a biochemical mechanism.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. Substituted phenyl includes phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates and bicarbonates, as well as aliphatic and primary, secondary and tertiary amines, aliphatic diamines and hydroxy alkylamines. Bases especially useful in the preparation of addition salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to increase libido, according to this invention, will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need of treatment from once to about three times each day, or more often as needed to effectively increase libido.

It is usually preferred to administer a compound of formula I in the form of an acid addition salt, as is customary in the administration of pharmaceuticals bearing a basic group, such as the piperidino ring. It is also advantageous to administer such a compound by the oral route to an aging human (e.g. a post-menopausal female). For such purposes the following oral dosage forms are available.

FORMULATIONS

In the formulations which follow, "Active ingredient" means a compound of formula I.

| Formulation 1: Gelatin Capsules  Hard gelatin capsules are prepared using the following: | |
|---|---|
| Ingredient | Quantity (mg/capsule) |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

| Ingredient | Quantity (mg/capsule) |
|---|---|
| Formulation 2: Raloxifene capsule | |
| Raloxifene | 1 |
| Starch, NF | 112 |
| Starch flowable powder | 225.3 |
| Silicone fluid 350 centistokes | 1.7 |
| Formulation 3: Raloxifene capsule | |
| Raloxifene | 5 |
| Starch, NF | 108 |
| Starch flowable powder | 225.3 |
| Silicone fluid 350 centistokes | 1.7 |
| Formulation 4: Raloxifene capsule | |
| Raloxifene | 10 |
| Starch, NF | 103 |
| Starch flowable powder | 225.3 |
| Silicone fluid 350 centistokes | 1.7 |
| Formulation 5: Raloxifene capsule | |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

| Formulation 6: Tablets | |
|---|---|
| Ingredient | Quantity (mg/tablet) |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

| Formulation 7: Tablets | |
|---|---|
| Ingredient | Quantity (mg/tablet) |
| Active ingredient | 0.1–1000 |
| Starch | 45 |
| Cellulose, microcrystalline | 35 |
| Polyvinylpyrrolidone  (as 10% solution in water) | 4 |

| Formulation 7: Tablets -continued | |
|---|---|
| Ingredient | Quantity (mg/tablet) |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

| Formulation 8: Suspensions | |
|---|---|
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

TEST PROCEDURES

Assay 1

Animals used are ovariectomized or ovariectomized-/adrenalectomized Sprague-Dawley rats (Specific Pathogen Free-Anticimex, Stockholm) weighing 250–300 gms. They are housed in a room maintained at a temperature of 24° C. under reversed lighting (10 hours dark). Food and water (or saline) are available ad libitum. A compound of the invention is administered to one group of rats, and the other group is maintained as a control, and behavioral observations are made by placing each female with 2 cage-adapted, sexually experienced males for a 5-minute period during which about 20 mounts occur. The following measures are recorded:

1. Proportion of mounts by the male which elicited a lordosis response—L/M;
2. Lordosis intensity measured on a 3 point scale;
3. Lordosis duration (in seconds);
4. Female acceptance ratio - No. of mounts divided by No. of refused mounting attempts + mounts, a measure of the female's willingness to accept the male when he attempts to mount her.

Activity of the compound is shown through positive impact on any one of the 4 observations, as compared to control.

Assay 2

Five to fifty women are selected for the clinical study. These women are post-menopausal, i.e., have ceased menstruating for between 6 and 12 months prior to the study's initiation, are in good general health, and suffer from self-described loss of libido especially noted after menopause. Because of the idiosyncratic and subjective nature of this symptom, the study has a placebo control group, i.e., the women are divided into two groups, one of which receive the active agent of this invention and the other receive's a placebo. Women in the test group receive between 50–200 mg of the drug per day by the oral route. They continue this therapy for 3–12 months. Accurate records are kept as to the level of libido of the women in both groups and at the end of the study these results are compared.

Activity of the compounds of the invention are illustrated by positive effects in at least one of the above assays.

We claim:

1. A method of increasing libido in postmenopausal women comprising administering to a female human in need of treatment an effective amount of a compound having the formula

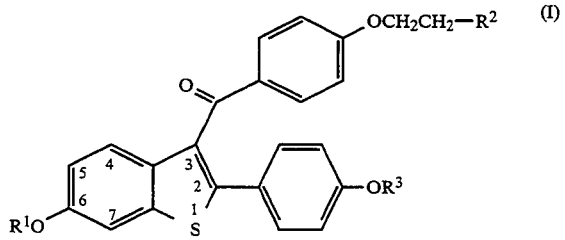

wherein $R^1$ and $R^3$ are independently hydrogen, $-CH_3$,

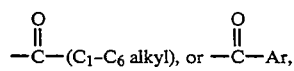

wherein Ar is optionally substituted phenyl;
$R^2$ is selected from the group consisting of pyrrolidine, hexamethyleneimino, and piperidino; or a pharmaceutically acceptable salt of solvate thereof.

2. The method of claim 1 wherein said compound is the hydrochloride salt thereof.

3. The method of claim 1 wherein said compound

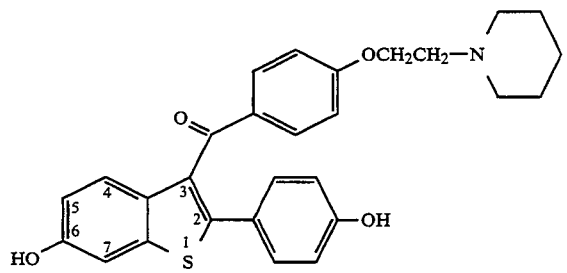

or its hydrochloride salt.

* * * * *